United States Patent [19]
Holsen et al.

[11] Patent Number: 5,443,271
[45] Date of Patent: Aug. 22, 1995

[54] AUTOMATED DRY DEPOSITION SAMPLER

[75] Inventors: Thomas M. Holsen, Oak Forest; Kenneth E. Noll, Glen Ellyn, both of Ill.

[73] Assignee: Illinois Institute of Technology, Chicago, Ill.

[21] Appl. No.: 77,615

[22] Filed: Jun. 15, 1993

[51] Int. Cl.⁶ .............................................. G01N 1/04
[52] U.S. Cl. .............................. 73/863.22; 73/864.71; 73/28.05; 73/170.17
[58] Field of Search .......... 73/863.22, 864.71, 863.21, 73/28.04, 28.05, 28.06, 170.17, 170.25; 55/270

[56] References Cited

U.S. PATENT DOCUMENTS

| | | | |
|---|---|---|---|
| 2,973,642 | 3/1961 | Grinnell et al. | 73/863.22 |
| 3,479,869 | 11/1969 | Jugle | 73/170.25 |
| 3,620,078 | 11/1971 | Raynor . | |
| 3,633,405 | 1/1972 | Noll | 73/28.06 |
| 3,681,973 | 8/1972 | Ludwig | 73/28.06 |
| 3,914,979 | 10/1975 | Shofner | 73/28.05 |
| 4,133,202 | 1/1979 | Marple | 73/28.06 |
| 4,665,744 | 5/1987 | Smith | 73/170.17 |
| 4,764,186 | 8/1988 | Langer | 73/28.06 |
| 4,774,836 | 10/1988 | Davidson et al. | 73/28.04 |
| 4,827,779 | 5/1989 | Marple et al. | 73/863.22 |
| 4,932,254 | 6/1990 | Davidson et al. | 73/170.25 |

FOREIGN PATENT DOCUMENTS 3543489  6/1987  Germany ........................ 73/170.17

OTHER PUBLICATIONS

Raynor, Gilbert et al., "An Automatic Sequential Precipitation Sampler", 1979, pp. 149-155.
Noll et al., "Characterization of the Deposition of Particles from the Atmosphere to a Flat Plate", *Atmospheric Environment*, vol. 22, No. 7, pp. 1461-1468 (1988).
Noll et al., "Development of a Dry Deposition Model for Atmospheric Coarse Particles", *Atmospheric Environment*, vol. 23, No. 3, pp. 585-594 (1989).
McCready, D. I., "Wind Tunnel Modeling of Small Particle Deposition," *Aerosol Sci. Technol.*, vol. 5, pp. 301-312 (1986).
Noll et al., "Mass-Size Distribution and Dry Deposition Flux of Particles and Metals in Chicago", Air & Waste Management Association 85th Annual Meeting & Exhibition, Jun. 21-26, 1992, Kansas City, Mo., 92-69.17, pp. 1-16.
Fang, Guor Cheng, "A Study of Mass Size Distributions and Particle Deposition Velocities in Ambient Air", Chicago, Ill. (1992) (Thesis paper submitted to the Graduate School of the Illinois Institute of Technology) pp. 35, 36, 39, 50 and 52.

*Primary Examiner*—Hezron E. Williams
*Assistant Examiner*—Nashimya Ashraf
*Attorney, Agent, or Firm*—Speckman, Pauley & Fejer

[57] ABSTRACT

A dry deposition sampling apparatus having at least one thin dry deposition plate with sample collection film is maintained on a support structure which is rotatable about a vertical axis and has a vane to maintain the sharp leading edge of the dry deposition plate(s) headed into the wind. Covers are positioned over the sample collection films automatically upon commencement of precipitation and are automatically moved to a position exposing the sample collection films to the atmosphere upon cessation of precipitation. The duration of exposure of the collection films to the atmosphere is timed, thus providing a dry deposition sampling apparatus which may be left unattended for long periods of time.

22 Claims, 2 Drawing Sheets

AUTOMATED DRY DEPOSITION SAMPLER

BACKGROUND OF THE INVENTION

1. Field of the Invention

This invention relates to an automated dry deposition sampler for direct measurement of downward or upward flux of materials in the atmosphere during periods without precipitation.

2. Description of Related Art

There are two fundamentally different types of sampling of airborne materials: 1. sampling of concentrations of particles or chemical compounds in the air which measure in units of mass per volume; and 2. sampling of flux of particles or chemical compounds in the air which measurements have units of mass per area per time. The dry deposition sampler of this invention falls into the latter class.

A number of patents relate to samplers for measurement of airborne concentrations of particles: U.S. Pat. Nos. 3,914,979; 3,479,869 and 3,681,973 teach sampling devices having a wind vane to keep the device headed into the wind; slotted particle impactors are taught by U.S. Pat. No. 4,764,186 and multiple nozzle impactors are taught by U.S. Pat. No. 4,133,202; U.S. Pat. No. 3,620,078 teaches a roto-slide particle sampler having automatically opening shields to protect collection plates from wind compaction; U.S. Pat. No. 4,827,779 teaches a personal impactor having a porous impactor plate cartridge with a lightly oiled surface through which air is drawn by a pump; U.S. Pat. No. 2,973,642 teaches a rotatable sampler having a tacky adhesive surface; and U.S. Pat. No. 3,633,405 teaches a multi-stage rotary inertial impaction sampler.

U.S. Pat. Nos. 4,774,836 and 4,932,254 teach detectors for dry deposition measurement of flux of airborne materials. These patents teach a radially symmetrical airfoil-type surface having a flat circular surrogate sample collection surface mounted centrally on the top surface, the airfoil surface providing a laminar or transition boundary layer over the surrogate surface. The surrogate sampling surface may be coated with coating capable of retaining the contaminants. The structure forming the airfoil-type surface is supported by a post extending from the center of its bottom surface. The dry deposition detectors taught by these patents are limited to measurement of downward flux and cannot be used to measure upward flux, as may be desired in many cases. A further disadvantage of the dry deposition detectors taught by these patents is that they must be attended, that is, they must be removed and replaced or covered and uncovered by someone with time periods noted at each occasion of rain or snow. Thus, the dry deposition detectors taught by these patents cannot be left unattended for desired long periods of atmospheric sampling.

Wind tunnel testing of small particle deposition on flat plates has been reported by D. I. McCready, Wind Tunnel Modeling of Small Particle Deposition, Aerosol Sci. Technol., Vol. 5, pp. 301–312, (1986).

Study of deposition of particles from the atmosphere to single greased sample collectors on the upper and lower side of a single flat dry deposition plate having a wind vane attached directly to the singly dry deposition plate and a horizontal shield over the dry deposition plate has been reported by K. E. Noll, Fang, K. Y. P. and Watkins, L. A., Characterization of the Deposition of Particles from the Atmosphere to a Flat Plate, Atmospheric Environment, Vol. 22, No. 7, pp. 1461–1468, (1988). A dry deposition model for atmospheric coarse particles using sample collectors described in Noll, et al, supra, has been described by K. E. Noll and Fang, K. Y. P., Development of a Dry Deposition Model for Atmospheric Coarse Particles, Atmospheric Environment, Vol. 23, No. 3, pp. 585–594, (1989).

SUMMARY OF THE INVENTION

It is an object of this invention to provide an automated dry deposition sampler which may be left unattended for periods of atmospheric sampling.

It is another object of this invention to provide an automated dry deposition sampler which senses rain or snow, covers the sample collectors during periods of precipitation and uncovers the sample collectors upon cessation of the precipitation.

Yet another object of this invention is to provide an automated dry deposition sampler which indicates the time which the sample collectors have been exposed to the atmosphere.

Still another object of this invention is to provide an automated dry deposition sampler in which the sample collectors may be easily weighed before and after the sample collection period to obtain the total weight of the sample collected during a noted time period.

These objects are achieved by the dry deposition sampler of this invention having at least one thin dry deposition plate with substantially parallel horizontal plate surfaces and a sharp leading edge of less than about a 10° angle maintained substantially horizontal on an elongated support structure which is rotatable about a vertical axis. A vane means fixedly attached to the support structure maintains the sharp leading edge of the dry deposition plate headed into the wind. Collection means are removably mounted on at least the upper of the horizontal plate surfaces and have covering means capable of covering the collection means on at least the upper of the horizontal plate surfaces during periods of precipitation. The dry deposition sampler of this invention is automated by having precipitation sensing means sense commencement and cessation of periods of precipitation and controlled driving means which move the covering means into position covering the collection means upon commencement of precipitation and move the covering means into position exposing the collection means to the atmosphere upon cessation of precipitation. In one preferred embodiment, a single vane means is attached to the longitudinal center of the elongated support structure which is rotably mounted at its longitudinal center to a support pole. It is preferred to have a plurality of the dry deposition plates maintained in a substantially horizontal position on the elongated support structure and spaced a sufficient distance from each other so as to avoid sample collection interference. In one embodiment, one of the dry deposition plates is attached to each of the opposite end portions of the elongated support structure.

The automated dry deposition sampler has electronic control means which receives signals from a precipitation sensor upon commencement and cessation of precipitation and sends signals to driving means which move the covering means into position covering at least the collection means on the upper of the dry deposition plate surfaces upon commencement of precipitation and which move the covering means into position exposing the collection means to the atmosphere upon cessation of precipitation. The electronic control means may also have a timing means capable of recording the time of exposure of the collection means to the atmosphere.

In the dry deposition sampler of this invention, collection means may be mounted one the upper surface of the dry deposition plate to measure downward flux and on the lower surface of the dry position plate to measure upward flux. It is desirable that the collection means comprise a plurality of collection films having a retaining coating on their collection surface facing the atmosphere. The collection films are preferably retained in desired position on the surface of the dry deposition plate by an overlying collection film holder having openings of specified area exposing each of the collection surfaces to the atmosphere. The collection films may be weighed before and after the exposure period to easily ascertain the weight of material collected over the specified area of the opening.

BRIEF DESCRIPTION OF THE DRAWINGS

The above and other advantages of this invention will become apparent upon reading the detailed description of preferred embodiments in reference to the drawings, wherein.

DESCRIPTION OF PREFERRED EMBODIMENTS

Figure 1:
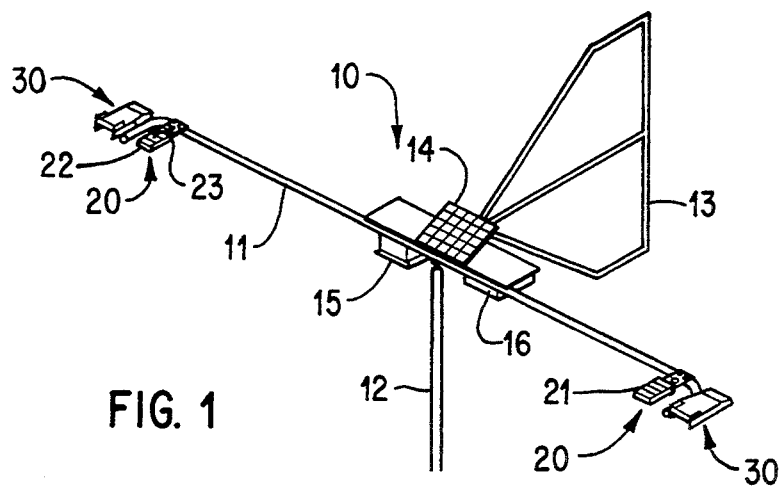
FIG. 1 is a simplified perspective view of an automated dry deposition sampler according to one embodiment of this invention.
Figure 2:
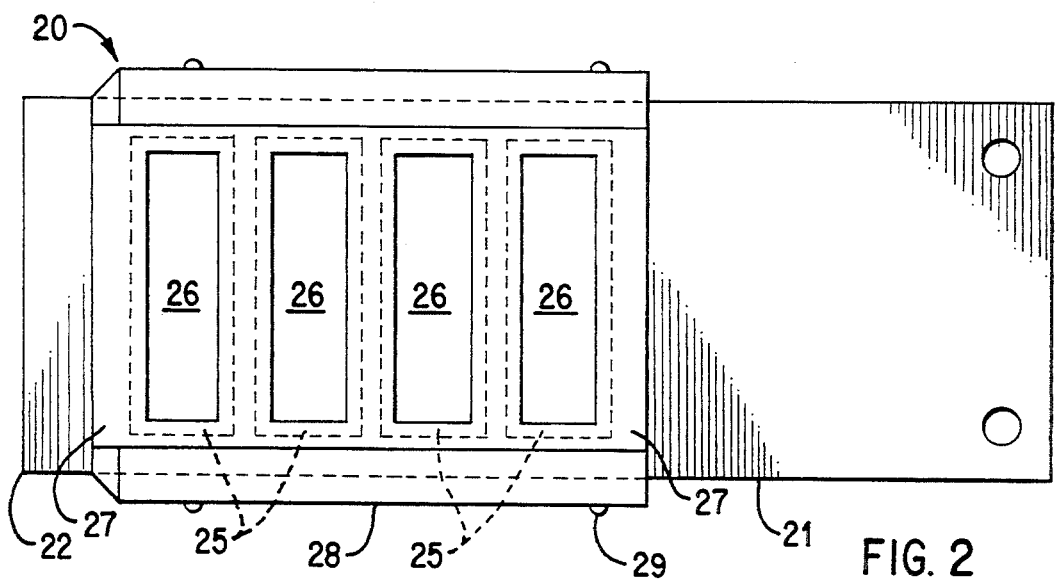
FIG. 2 is a top view of one embodiment of a dry deposition plate for use in the automated dry deposition sampler of this invention.
Figure 3:
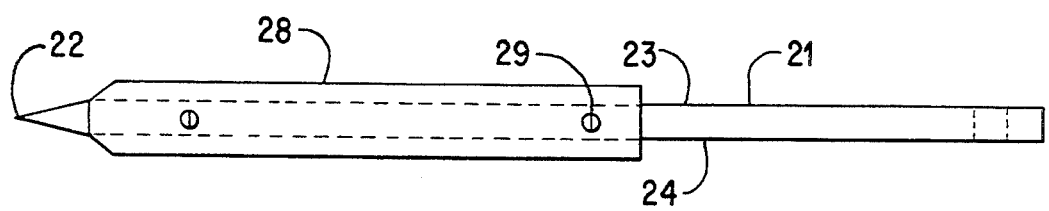
FIG. 3 is a side view of the dry deposition plate shown in FIG. 2.
Figure 4:
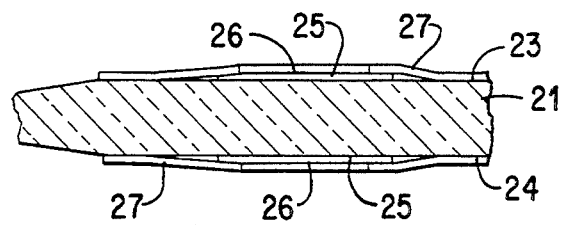
FIG. 4 is an enlarged cross-sectional view through a dry deposition plate showing a collection film and collection film holder.

One embodiment of the automated dry deposition sampler of this invention is shown in a simplified perspective view in FIG. 1 as 10. The automated dry deposition sampler 10 has sample detectors 20 each comprising a thin dry deposition plate 21 having substantially parallel horizontal plate surfaces, upper surface 23 and lower surface 24 and a sharp leading edge 22 of less than about 10°, as best seen in FIG. 3. Each of the dry deposition plates 21 are maintained substantially horizontal on elongated support structure 11 which is rotatable about a vertical axis. In the embodiment shown in FIG. 1, elongated support structure 11 is rotably mounted at its longitudinal center to support pole 12. Vane means 13 is rigidly attached to support structure 11 to maintain sharp leading edges 22 of dry deposition plates 21 headed into the wind. Preferably, vane means 13 is a single vane means attached to the longitudinal center of elongated support structure 11. Sample detector 20 has collection means removably mounted on at least the upper horizontal plate surface 23, and preferably, on both upper horizontal plate surface 23 and lower horizontal plate surface 24 to measure downward and upward flux, respectively. As best seen in FIGS. 2 and 3, the collection means preferably comprises a plurality of collection films 25 having a retaining coating on their collection surfaces 26. Collection films 25 are retained in desired position by an overlying collection film holder 27 retained on dry deposition plate 21 by edge channels 28 which are retained firmly against deposition plate 21 by screws 29. Covering means 30 is capable of covering the collection means on at least upper horizontal plate surface 23 during periods of precipitation.

Figure 5:
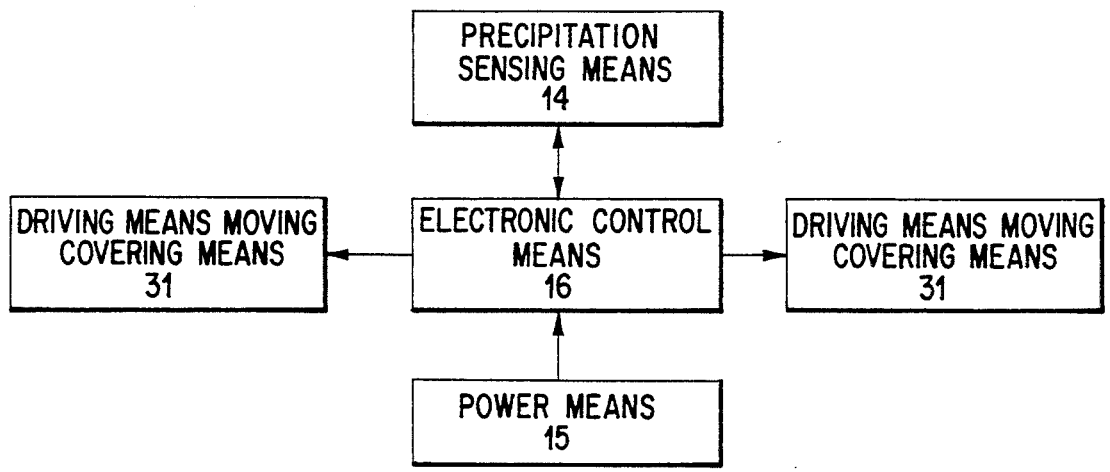
FIG. 5 is a simplified schematic diagram illustrating operation of an electronic control means according to one embodiment of this invention.

Precipitation sensing means 14 is any suitable means for sensing commencement and cessation of periods of precipitation, such as rain or snow, and controlling driving means moving covering means 30 into position covering the collection means upon commencement of precipitation and moving the covering means into position exposing the collection means to the atmosphere upon cessation of precipitation. In preferred embodiments, as shown schematically in FIG. 5, precipitation sensing means 14 signals electronic control means 16 upon commencement and cessation of precipitation. Electronic control means 16 signals driving means 31 moving covering means 30 into position covering the collection means on upper horizontal plate surfaces 23 upon commencement of precipitation and moving the covering means into position exposing the collection means upon cessation of precipitation. Electronic control means 16 preferably comprises timing means to record time of exposure of the collection means to the atmosphere. Electronic control means 16 may also include a temperature sensing means which initiates a signal activating heaters for precipitation sensing means 14 to render the sensing means, which is dependent upon moisture for signal activation, more sensitive at freezing temperatures by melting ice or snow. The precipitation sensing means, of the type dependent upon moisture for signal activation, is also preferably at least intermittently heated during precipitation to evaporate water so that cessation of the precipitation may be most accurately detected. As shown in FIG. 1, power means 15, such as batteries, precipitation sensing means 14 and electronic control means 16 may all be mounted on elongated support structure 11 to form a self-contained unit. Specific components for sensing means 14 and electronic control means 16 do not form a part of this invention and may be widely varied, as will be readily apparent to one skilled in the art. Likewise, specific components for driving means 31 are not a part of this invention and may include a variety of electro-mechanical configurations which will be apparent to one skilled in the art upon reading this description.

The dry deposition plate used in the apparatus of this invention is similar to the one described by Noll, Fang and Watkins, supra, except that it has a plurality of collection films 25 on each the upper and lower face of the dry deposition plate. The plurality of adjacent collection films results in larger mass collection for chemical analysis while having small individual films which may be easily and accurately weighed. The plurality of adjacent collection films also allows averaging of the individual collection results to arrive at a more accurate measurement and elimination of a single spurious collection result. We have found that a plurality of collection films may be placed on the upper and lower surfaces of a dry deposition plate without causing interference with sample collection, each providing typical sample collection. The dry deposition plate, collection film and collection film holder should be of materials which do not interfere electrically or chemically with the dry deposition sampling. Further description of the dry deposition plate, its construction, materials and manner of use are more fully set forth by K. E. Noll, Holsen, T. M., Fang, G. C. and Lin, J. M., Mass-Size Distribution and Dry Deposition Flux of Particles and Metals in Chicago, 85th Annual Meeting & Exhibition, Air & Waste Management Association, Kansas City, Mo., Jun. 21–26, 1992 and by G. C. Fang, A Study of Mass Size Distributions and Particle Deposition Velocities in Ambient Air, PhD Thesis, Illinois Institute of Technology, pp. 35–36, 39, 50 and 52, August, 1992, both of which are incorporated herein by reference.

The arrangement of a plurality of dry deposition plates on an elongated support structure which is rotatable by vane means, according to the present invention, allows collection of a plurality of samples under substantially similar conditions for obtaining larger mass collection and increasing accuracy. Any desired number of dry deposition plates may be mounted on the elongated support structure as long as they are spaced a sufficient distance from each other to avoid sample collection interference and consistent with adequate rigidity of the support structure. The elongated support structure may be a metallic tubular material or any other shape which provide rigidity and does not interfere with sample collection. The rotatable support structure provides mounting for covering means and driving means to operate the covering means.

The elongated support structure may also provide mounting for a precipitation sensor, electronic control means and power means for operation of an automated self-contained unit. However, it will be appreciated that a non-attached precipitation sensor and electronic control means may be used with only power means sufficient for operation of the driving means being mounted on the support structure. The support structure is shown, in FIG. 1, to be rotatably mounted to a support pole from its bottom. It should be apparent that the support structure may be rotably mounted to a number of different support pole configurations, such as at the bottom of a depending pole or on a horizontal pole or other suitable structure, all of which is intended to be included in this invention. The elongated support structure may have arms extending therefrom to provide mounting for covering means, as shown in FIG. 1 with arms extending from each end region. Similar arms may also extend from central regions of an elongated support structure. Any other mounting for the covering means may be used which permits covering and uncovering of the sample detectors without interference to the sample collection. As shown in FIG. 1, covering means 30 may rotate about or with arms of the support structure to provide desired covering for the sample collectors. Movement of the covering means may be achieved by individual drive means driving each covering means, such as by use of separate servo-mechanisms, or a plurality of covering means may be driven through mechanical linkages from a single drive means, as will be apparent upon reading of this description. All such means are meant to be included in this invention. The covering means should be of suitable shape and size to cover and protect the upper surface of the dry deposition plate from precipitation. As shown in FIG. 1, the covering means is rectangular and slightly larger than the dry deposition plate with its front and side edges turned to depend downwardly over the sides of the dry deposition plate when in covering position to prevent wind blown precipitation from landing on the surface of the sample collectors.

While vane means 13 is shown in FIG. 1 as a single vane, it is readily apparent that multiple vanes and vanes of various shapes may be used as long as the vanes are rigidly attached to the elongated support structure and sufficient to maintain sharp leading edges of the dry deposition plates headed into the wind without interference to sample collection.

One preferred embodiment of an automated dry deposition sampler, as shown in FIG. 1, has extended arms spaced 157.5 cm apart at opposite ends of the elongated support structure which has a single vane 122 cm high attached to its longitudinal center. The dry deposition collection plates are made of polyvinyl chloride 0.65 cm thick, 7.6 cm wide and 21.5 cm long with a leading edge of <10° angle. Four Mylar sample collection films 7.6 cm by 2.5 cm each coated with 8 mg Apezion L grease, thickness about 8 $\mu$m, were held in place on the top and bottom of each dry deposition collection plate by a 5 mil thick Teflon collection film holder secured along each side by polyacrylic edge channels fastened to the edge of the dry deposition plate. The collection film holder had four 5.7 cm by 1.8 cm cutouts indexed with the sample collection films providing 41.04 cm2 exposed sample collection surface on each side of each dry deposition collection plate. The rain sensor was a circuit board about 20 cm by 20 cm covered with metallic projections spaced about 1 mm apart. A raindrop falls on the board connecting two of the metallic projections closing an electrical circuit causing a change in resistance which is sensed by an electronic control unit. The electronic control unit then sends an electrical signal activating an electric motor at each covering means moving each covering means into covering position which is set by magnetic limit switches and a backup circuit sensor. The back of the sensor is covered with resistors and insulation to provide heat to the board when 1) a rain drop is sensed or 2) when the temperature is below about 5° C. After precipitation is evaporated by the heat, the circuit remains open, indicating cessation of the precipitation, which is sensed by the electronic control unit which then sends a signal activating the electric motor at each covering means moving the covering means into open position exposing the dry deposition plate to the atmosphere. The control unit microprocessor also contains a timer which records the total time the dry deposition plates have been installed on the sampler and the time that they have been exposed to the atmosphere. Suitable electronic control means will be apparent to one skilled in the art.

The automated dry deposition sampler of this invention may be loaded with a plurality of collection films, which have been previously weighed, and left unattended in field operation for desired long periods of time without being attended, particularly with respect to being taken inside or covered upon commencement of precipitation and being replaced in sampling position upon cessation of precipitation by an attendant, as required by prior art dry deposition samplers.

While in the foregoing specification this invention has been described in relation to certain preferred embodiments thereof, and many details have been set forth for purpose of illustration it will be apparent to those skilled in the art that the invention is susceptible to additional embodiments and that certain of the details described herein can be varied considerably without departing from the basic principles of the invention.

We claim:
1. An automated dry deposition sampler comprising: at least one thin dry deposition plate having substantially parallel upper and lower horizontal plate surfaces and a sharp leading edge of less than about a 10° angle to said horizontal plate surfaces; said dry deposition plate mounted substantially horizontal on an elongated support structure, said support structure mounted to rotate about a vertical axis; wind vane means mounted fixedly to said support structure to maintain said sharp leading edge of said dry deposition plate headed into a wind; collection means mounted removably on at least said upper horizontal plate surface of said dry deposition plate; movable covering means covering said collection means on at least said upper horizontal plate surface in a first position and exposing said collection means to the atmosphere in a second position; precipitation sensing means sensing commencement and cessation of periods of precipitation; and driving means controlled by said precipitation sensing means moving said covering means into said first position covering said collection means upon commencement of precipitation and moving said covering means into said second position exposing said collection means to the atmosphere upon cessation of precipitation.

2. An automated dry deposition sampler according to claim 1 wherein said wind vane means comprises a single vane attached to the longitudinal center of said elongated support structure and said elongated support structure is mounted rotably at said longitudinal center to a support pole.

3. An automated dry deposition sampler according to claim 2 having a plurality of dry deposition plates mounted substantially horizontal on said elongated support structure and spaced a sufficient distance from each other to avoid sample collection interference.

4. An automated dry deposition sampler according to claim 3 comprising said precipitation sensing means signalling an electronic control means upon commencement and cessation of precipitation, said electronic control means signalling said driving means moving said covering means into said first position covering at least said collection means on each said upper horizontal plate surface upon commencement of precipitation and signalling said driving means moving said covering means into said second position exposing each said collection means to the atmosphere upon cessation of precipitation.

5. An automated dry deposition sampler according to claim 4 comprising timing means signalled by said precipitation sensing means upon said commencement and cessation of precipitation to record time of exposure of said collection means to the atmosphere.

6. An automated dry deposition sampler according to claim 1 wherein said collection means are mounted on both said upper and said lower horizontal plate surfaces.

7. An automated dry deposition sampler according to claim 6 wherein said collection means comprises a plurality of collection films each having a retaining coating on a collection surface facing the atmosphere, said collection films retained in desired position by an overlying collection film holder having openings exposing said collection surfaces.

8. An automated dry deposition sampler according to claim 7 comprising said precipitation sensing means signalling an electronic control means upon commencement and cessation of precipitation, said electronic control means signalling said driving means moving said covering means into said first position covering said collection means on said upper horizontal plate surface upon commencement of precipitation and signalling said driving means moving said covering means into said second position exposing said collection means upon cessation of precipitation.

9. An automated dry deposition sampler according to claim 1 wherein one said dry deposition plate is mounted to each end of said elongated support structure, said dry deposition plates spaced a sufficient distance from each other to avoid sample collection interference.

10. An automated dry deposition sampler according to claim 9 wherein said wind vane means comprises a single vane attached to the longitudinal center of said elongated support structure and said elongated support structure is mounted rotably at said longitudinal center to a support pole.

11. An automated dry deposition sampler according to claim 10 comprising said precipitation sensing means signalling an electronic control means upon commencement and cessation of precipitation, said electronic control means signalling driving means moving said covering means into said first position covering said collection means on each said upper horizontal plate surface upon commencement of precipitation and signalling driving means moving said covering means into said second position exposing each said collection means to the atmosphere upon cessation of precipitation.

12. An automated dry deposition sampler according to claim 11 comprising timing means signalled by said precipitation sensing means upon said commencement and cessation of precipitation to record time of exposure of said collection means to the atmosphere.

13. An automated dry deposition sampler according to claim 9 wherein said collection means are mounted on both said upper and said lower horizontal plate surfaces of each plate.

14. An automated dry deposition sampler according to claim 13 wherein said collection means comprises a plurality of collection films each having a retaining coating on a collection surface facing the atmosphere, said collection films retained in desired position by an overlying collection film holder having openings exposing said collection surfaces.

15. An automated dry deposition sampler according to claim 13 comprising said precipitation sensing means signalling an electronic control means upon commencement and cessation of precipitation, said electronic control means signalling said driving means moving said covering means into said first position covering said collection means on each said upper horizontal plate surface upon commencement of precipitation and signalling said driving means moving said covering means into said second position exposing said collection means upon cessation of precipitation.

16. In a dry deposition samples of the type having at least one thin dry deposition plate having substantially parallel upper and lower horizontal plate surfaces and a sharp leading edge of less than about a 10° angle to said horizontal plate surfaces headed into a wind with collection means removably mounted on at least said upper horizontal plate surface, the improvement comprising: said thin dry deposition plate mounted substantially horizontal on an elongated support structure, said support structure mounted rotably about a vertical axis and has a wind vane attached thereto to maintain said sharp leading edge headed into the wind; movable covering means covering said collection means on at least said upper horizontal plate surface in a first position and exposing said collection means to the atmosphere in a second position; precipitation sensing means sensing commencement and cessation of periods of precipitation; and driving means controlled by said precipitation sensing means moving said covering means into said first position covering said collection means upon commencement of precipitation and moving said covering means into said second position exposing said collection means to the atmosphere upon cessation of precipitation.

17. In a dry deposition sampler according to claim 16 wherein said wind vane means comprises a single vane attached to the longitudinal center of said elongated support structure and said elongated support structure is mounted rotably at said longitudinal center to a support pole and a plurality of dry deposition plates are mounted substantially horizontal on said elongated support structure and spaced a sufficient distance from each other to avoid sample collection interference.

18. In a dry deposition sampler according to claim 17 comprising said precipitation sensing means signalling an electronic control means upon commencement and cessation of precipitation, said electronic control means signalling said driving means moving said covering means into said first position covering at least said collection means on each said upper horizontal plate surface upon commencement of precipitation and signalling said driving means moving said covering means into said second position exposing said collection means to the atmosphere upon cessation of precipitation.

19. A dry deposition sampler according to claim 18 comprising timing means signalled by said precipitation sensing means upon said commencement and cessation of precipitation to record time of exposure of said collection means to the atmosphere.

20. In a dry deposition sampler according to claim 19 wherein said collection means are mounted on both said upper and said lower horizontal plate surfaces of each plate.

21. In a dry deposition sampler according to claim 20 wherein said collection means comprises a plurality of collection films each having a retaining coating on a collection surface facing the atmosphere, said collection films retained in desired position by an overlying collection film holder having openings exposing said collection surfaces.

22. A dry deposition sampler according to claim 21 comprising Said precipitation sensing means signalling an electronic control means upon commencement and cessation of precipitation, said electronic control means signalling said driving means moving said covering means into said first position covering said collection means on each said upper horizontal plate surface upon commencement of precipitation and signalling said driving means moving said covering means into said second position exposing said collection means upon cessation of precipitation.

\* \* \* \* \*